US012648592B2

(12) United States Patent
Huang

(10) Patent No.: US 12,648,592 B2
(45) Date of Patent: Jun. 9, 2026

(54) VAPORIZATION ASSEMBLY AND ELECTRONIC VAPORIZATION DEVICE

(71) Applicant: Jiangmen Moore Technology., Ltd, Jiangmen (CN)

(72) Inventor: Yongrui Huang, Jiangmen (CN)

(73) Assignee: Jiangmen Moore Technology., Ltd, Jiangmen (CN)

( * ) Notice: Subject to any disclaimer, the term of this patent is extended or adjusted under 35 U.S.C. 154(b) by 364 days.

(21) Appl. No.: 18/081,389

(22) Filed: Dec. 14, 2022

(65) Prior Publication Data

US 2023/0210187 A1 Jul. 6, 2023

(30) Foreign Application Priority Data

Dec. 30, 2021 (CN) .......................... 202123418258.8

(51) Int. Cl.
*A24F 40/40* (2020.01)
*A24F 40/10* (2020.01)
(Continued)

(52) U.S. Cl.
CPC .............. *A24F 40/40* (2020.01); *A24F 40/10* (2020.01); *A24F 40/485* (2020.01); *A61M 11/042* (2014.02); *A61M 15/06* (2013.01)

(58) Field of Classification Search
CPC ...................................................... A24F 40/10
See application file for complete search history.

(56) References Cited

U.S. PATENT DOCUMENTS 10,548,351 B2 * 2/2020 Brammer ................ A24F 40/50
2016/0213065 A1 7/2016 Wensley et al.
(Continued)

FOREIGN PATENT DOCUMENTS

CN 215075476 U * 12/2021
JP 2018504926 A 2/2018
(Continued)

OTHER PUBLICATIONS

Translation of CN 215075476 U (Year: 2021).*
(Continued)

*Primary Examiner* — Michael H. Wilson
*Assistant Examiner* — Michael Patrick Mullen
(74) *Attorney, Agent, or Firm* — Leydig, Voit & Mayer, Ltd.

(57) ABSTRACT
A vaporization assembly includes: a vaporization base having a mounting cavity and an air outlet; a vaporization core arranged in the mounting cavity and cooperating with the vaporization base to define and form a vaporization cavity; a first airflow channel arranged in the vaporization base in a first direction, an air inlet end of the first airflow channel being in communication with the vaporization cavity; and a second airflow channel arranged in the vaporization base in a second direction intersecting with the first direction, an air outlet end of the second airflow channel being in communication with the air outlet, an air inlet end of the second airflow channel being in communication with an air outlet end of the first airflow channel. A corner between the air inlet end of the second airflow channel and the air outlet end of the first airflow channel is a smooth transition corner.

17 Claims, 5 Drawing Sheets

(51) Int. Cl.
    *A24F 40/485*         (2020.01)
    *A61M 11/04*         (2006.01)
    *A61M 15/06*         (2006.01)

(56)             References Cited

U.S. PATENT DOCUMENTS

| | | |
|---|---|---|
| 2021/0084976 A1 | 3/2021 | Xu et al. |
| 2022/0218038 A1* | 7/2022 | Lei ........................ A24F 40/485 |

FOREIGN PATENT DOCUMENTS

| | | |
|---|---|---|
| KR | 1020180065970 A | 6/2018 |
| WO | 2021062781 A1 | 4/2021 |
| WO | 2021098421 A1 | 5/2021 |

OTHER PUBLICATIONS

Japanese Patent Office, Notice of Reasons for Refusal in Japanese Patent Application No. 2022-180689 (Dec. 5, 2023).

European Patent Office, Search Report in European Patent Application No. 22215817.2 (May 31, 2023).

Korean Intellectual Property Office, Office Action in Korean Patent Application No. 10-2022-0151451 (Jan. 24, 2025).

European Patent Office, Office Action in European Patent Application No. 22215817.2 (Oct. 21, 2025).

Korean Patent Office, Notice of Allowance European Patent Application No. 10-2022-0151451 (Sep. 3, 2025).

* cited by examiner

200

252

A

251

213

214

200

20

VAPORIZATION ASSEMBLY AND ELECTRONIC VAPORIZATION DEVICE

CROSS-REFERENCE TO PRIOR APPLICATION

Priority is claimed to Chinese Patent Application No. 202123418258.8, filed on Dec. 30, 2021, the entire disclosure of which is hereby incorporated by reference herein.

FIELD

The present invention relates to the field of vaporization device technologies, and in particular, to a vaporization assembly and an electronic vaporization device.

BACKGROUND

An electronic vaporization device generates an aerosol by vaporizing an aerosol-forming substrate, and a user inhales the aerosol to achieve the objective of obtaining effective substances in the aerosol-forming substrate.

Under the action of an inhaling force of the existing electronic vaporization device, the aerosol is transmitted through an airflow channel and collected into a central air outlet channel, and is then inhaled into the mouth of the user. However, in a process of transmitting the aerosol in the airflow channel, the aerosol is prone to be scattered in a portion shown in a dotted circle A in FIG. 1 to form an eddy current. As a result, the vapor cannot be completely taken away by inhaling, and condensate remains on the airflow channel. After the condensate accumulates to a certain extent, there is a liquid leakage phenomenon, and finally the leaked liquid may be inhaled into the mouth of the user, reducing the use experience of the user.

SUMMARY

In an embodiment, the present invention provides a vaporization assembly, comprising: a vaporization base comprising a mounting cavity and an air outlet; a vaporization core arranged in the mounting cavity and cooperating with the vaporization base to define and form a vaporization cavity; a first airflow channel arranged in the vaporization base in a first direction, an air inlet end of the first airflow channel being in communication with the vaporization cavity; and a second airflow channel arranged in the vaporization base in a second direction intersecting with the first direction, an air outlet end of the second airflow channel being in communication with the air outlet, an air inlet end of the second airflow channel being in communication with an air outlet end of the first airflow channel, wherein a corner between the air inlet end of the second airflow channel and the air outlet end of the first airflow channel comprises a smooth transition corner.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
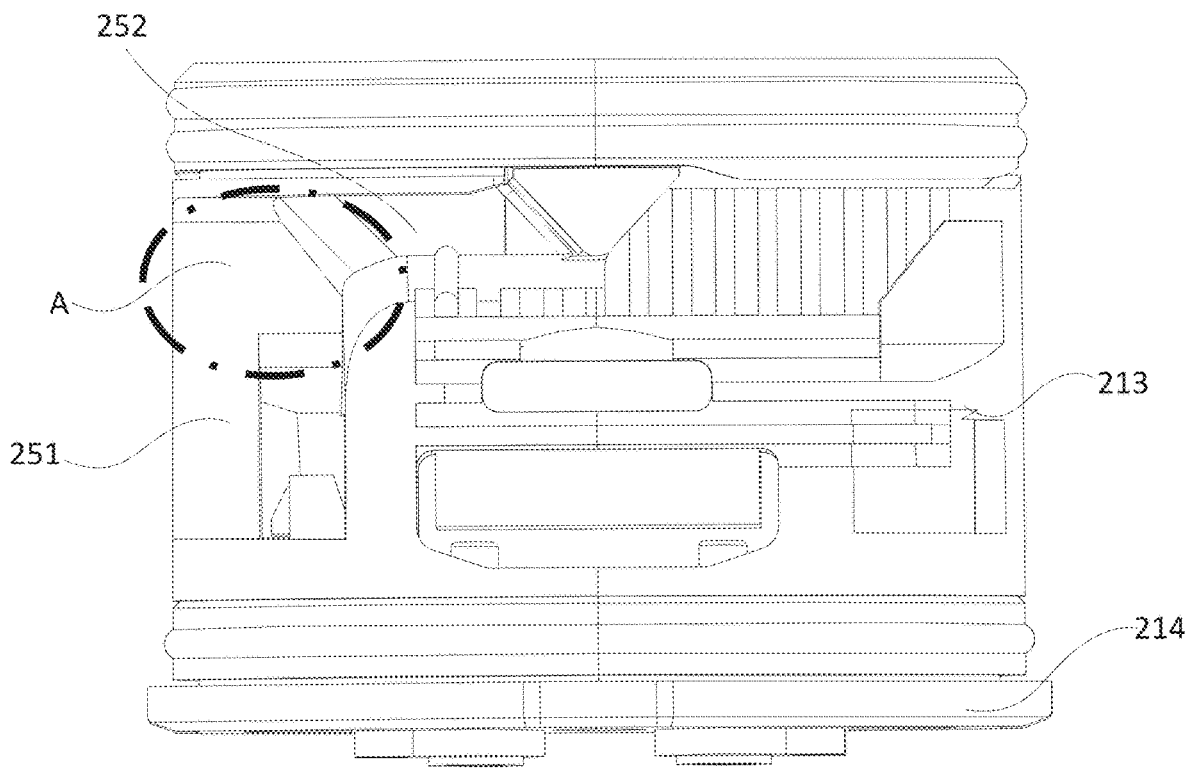
FIG. 1 is a schematic structural diagram of a partial area of a vaporization assembly in the related art.

In an embodiment, the present invention provides a vaporization assembly for the problem of poor user experience when a user uses the existing electronic vaporization device, including:

a vaporization base, including a mounting cavity and an air outlet;

a vaporization core, arranged in the mounting cavity, and cooperating with the vaporization base to define and form a vaporization cavity;

a first airflow channel, arranged in the vaporization base in a first direction and an air inlet end of the first airflow channel being in communication with the vaporization cavity; and a second airflow channel, arranged in the vaporization base in a second direction intersecting with the first direction and an air outlet end of the second airflow channel being in communication with the air outlet, and an air inlet end of the second airflow channel being in communication with an air outlet end of the first airflow channel, where a corner between the air inlet end of the second airflow channel and the air outlet end of the first airflow channel is a smooth transition corner.

In one of the embodiments, a smooth rounded corner is formed between a central axis of the first airflow channel and a central axis of the second airflow channel.

In one of the embodiments, the vaporization assembly further includes a capillary liquid absorbing structure, where the capillary liquid absorbing structure is arranged on the vaporization base and is in communication with the second airflow channel; and accumulated liquid in the second airflow channel flows into the capillary liquid absorbing structure and is collected by the capillary liquid absorbing structure when an inhaling action occurs at the air outlet.

In one of the embodiments, the capillary liquid absorbing structure includes at least one first capillary groove, and the plurality of first capillary grooves are spaced apart on the vaporization base in the first direction.

In one of the embodiments, the capillary liquid absorbing structure includes at least one second capillary groove, and the second capillary grooves are spaced apart on the vaporization base in the second direction.

In one of the embodiments, the vaporization assembly further includes a liquid guide structure, where the liquid guide structure is arranged on the vaporization base, and the accumulated liquid in the second airflow channel flows into the capillary liquid absorbing structure through the liquid guide structure.

In one of the embodiments, the liquid guide structure includes at least one airflow guide groove, a liquid inlet end of the liquid guide structure is in communication with the second airflow channel, and a liquid outlet end of the airflow guide groove is in communication with the capillary liquid absorbing structure.

In one of the embodiments, the vaporization assembly further includes a vaporization housing, where the vaporization housing includes an accommodating cavity, and the vaporization base and the vaporization core are accommodated in the accommodating cavity; and an air outlet channel is further provided in the vaporization housing, and the air outlet channel is in communication with the outside and the air outlet. In one of the embodiments, the vaporization base includes a vaporization top base and a vaporization bottom base, the vaporization top base and the vaporization bottom base cooperate together to form the mounting cavity, the vaporization core is arranged in the mounting cavity, the vaporization core cooperates with a cavity wall of the mounting cavity to define and form the vaporization cavity, and the air outlet is provided on the vaporization top base.

In one of the embodiments, the vaporization assembly further includes:

a first seal portion, sealedly connected between an outer side wall of the vaporization top base and an inner side wall of the vaporization housing; and a second seal portion, sealedly connected between an outer side wall of the vaporization bottom base and an inner side wall of the vaporization housing.

According to another aspect of this application, an electronic vaporization device is further provided, including a vaporization assembly and a power supply assembly electrically connected to the vaporization assembly; and the vaporization assembly is the vaporization assembly as described above.

In the vaporization assembly and electronic vaporization device, in an inhaling process, that is, in a process in which the aerosol flows from the vaporization cavity to the air outlet, the aerosol can implement a smooth turning at a communication portion between the air outlet end of the first airflow channel and the air inlet end of the second airflow channel, thereby preventing the aerosol from forming an eddy current or liquid leakage due to sharp turning, and improving the inhaling experience of the user.

200. Vaporization assembly; 20. vaporization housing; 201. accommodating cavity; 202. air outlet channel; 203. liquid storage cavity; 21. vaporization base; 211. mounting cavity; 212. air outlet; 213. vaporization top base; 214. vaporization bottom base; 215. vaporization cavity; 216. liquid flowing channel; 22. vaporization core; 241. first seal portion; 242. second seal portion; 251. first airflow channel; 252. second airflow channel; 27. capillary liquid absorbing structure; 271. first capillary groove; and 272. second capillary groove.

To make the foregoing objects, features and advantages of this application more comprehensible, detailed description is made to specific implementations of this application below with reference to the accompanying drawings. In the following description, many specific details are provided to facilitate a full understanding of this application. However, this application may alternatively be implemented in other manners different from those described herein, and a person skilled in the art may make similar modifications without departing from the content of this application. Therefore, this application is not limited to the embodiments disclosed below.

In the description of this application, it should be understood that orientation or position relationships indicated by the terms such as "center", "longitudinal", "transverse", "length", "width", "thickness", "on", "below", "front", "back", "left", "right", "vertical", "horizontal", "top", "bottom", "inside", "outside", "clockwise", "anticlockwise", "axial", "radial", and "circumferential" are based on orientation or position relationships shown in the accompanying drawings, and are used only for ease and brevity of illustration and description, rather than indicating or implying that the mentioned apparatus or component needs to have a particular orientation or needs to be constructed and operated in a particular orientation. Therefore, such terms should not be construed as limiting of this application.

In addition, the terms "first" and "second" are used merely for the purpose of description, and shall not be construed as indicating or implying relative importance or implying a quantity of indicated technical features. Therefore, features defining "first" and "second" can explicitly or implicitly include at least one of the features. In description of this application, "multiple" means at least two, such as two and three unless it is specifically defined otherwise.

In this application, it should be noted that unless otherwise clearly specified and limited, the terms "mounted", "connected", "connection", and "fixed" should be understood in a broad sense. For example, a connection may be a fixed connection, a detachable connection, or an integral connection; may be a mechanical connection or an electrical connection; may be a direct connection or an indirect connection by means of an intermediate medium; or may be internal communication between two elements or interaction relationship between two elements, unless otherwise clearly limited. A person of ordinary skill in the art may understand the specific meanings of the foregoing terms in this application according to specific situations.

In this application, unless explicitly specified or limited otherwise, a first characteristic "on" or "under" a second characteristic may be the first characteristic in direct contact with the second characteristic, or the first characteristic in indirect contact with the second characteristic by using an intermediate medium. In addition, the first feature being located "above" the second feature may be the first feature being located directly above or obliquely above the second feature, or may simply indicate that the first feature is higher in level than the second feature. The first feature "under", "below" and "down" the second feature may be that the first feature is directly below or obliquely below the second feature, or simply indicates that a horizontal height of the first feature is less than that of the second feature.

It should be noted that, when a component is referred to as "being fixed to" or "being arranged on" another component, the component may be directly on the another component, or there may be an intermediate component. When one component is considered as "being connected to" another component, the component may be directly connected to the another component, or an intermediate component may simultaneously exist. The terms "vertical", "horizontal", "upper", "lower", "left", "right", and similar expressions used in this specification are merely used for an illustrative purpose, and do not represent the only implementation.

The vaporization assembly and the electronic vaporization device of this application are described below with reference to the accompanying drawings.

Figure 2:
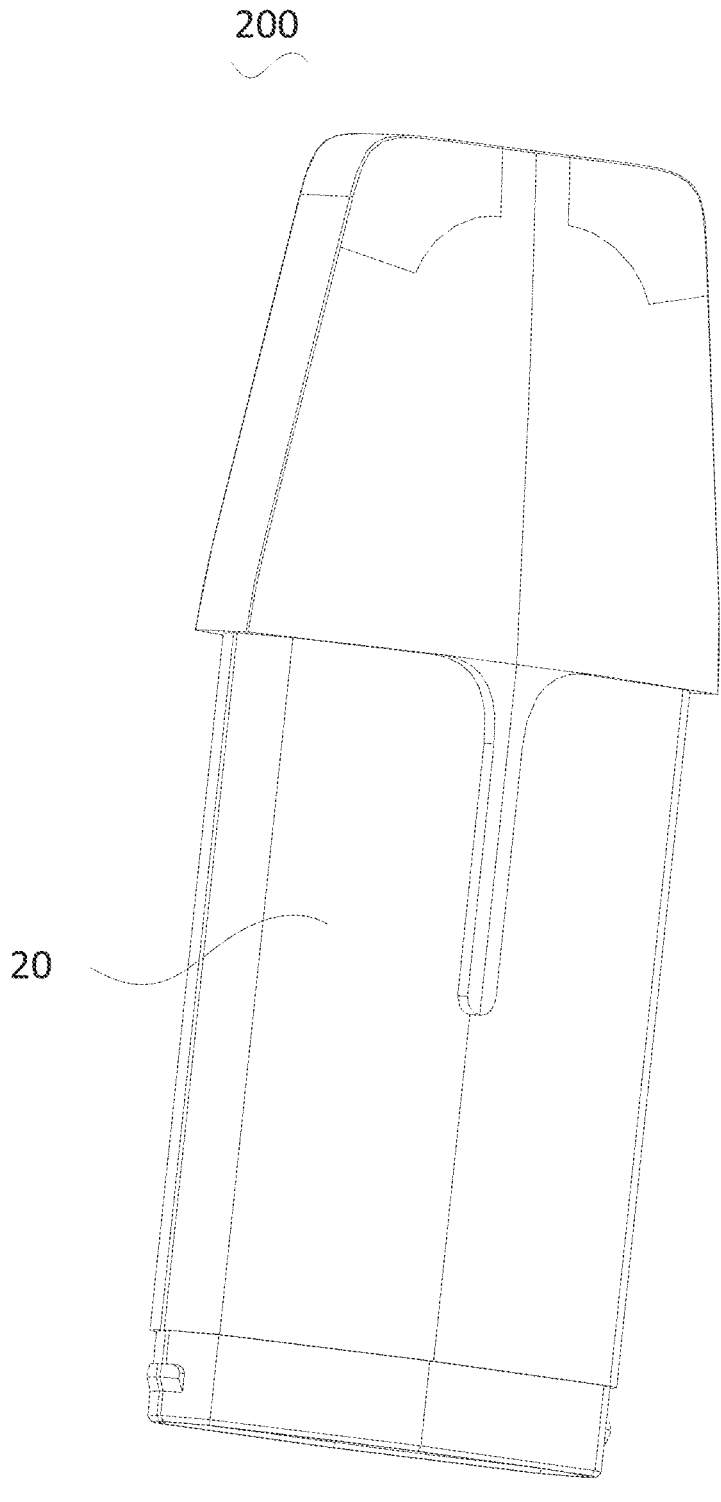
FIG. 2 is a schematic structural diagram of a vaporization assembly according to an embodiment of this application.

Referring to FIG. 2, the electronic vaporization device disclosed in at least one embodiment of this application includes a vaporization assembly 200 and a power supply assembly electrically connected to the power supply assembly 200. The vaporization assembly 200 is configured to store a liquid aerosol-generation substrate and vaporize the aerosol-generation substrate to form an aerosol that can be inhaled by the user. The liquid aerosol-generation substrate can be a liquid substrate such as liquid medicinal, plant grass liquid, or the like. The vaporization assembly 200 can be used in different fields, such as medical treatment, electronic aerosolization, or the like. A power source assembly includes components such as a battery, and the battery is configured to supply power to the vaporization assembly 200, so that the vaporization assembly 200 can vaporize the aerosol-generation substrate to form an aerosol. The vaporization assembly 200 and the power source assembly may be integrally arranged, or may be detachably connected, and can be designed according to specific needs.

Figure 3:
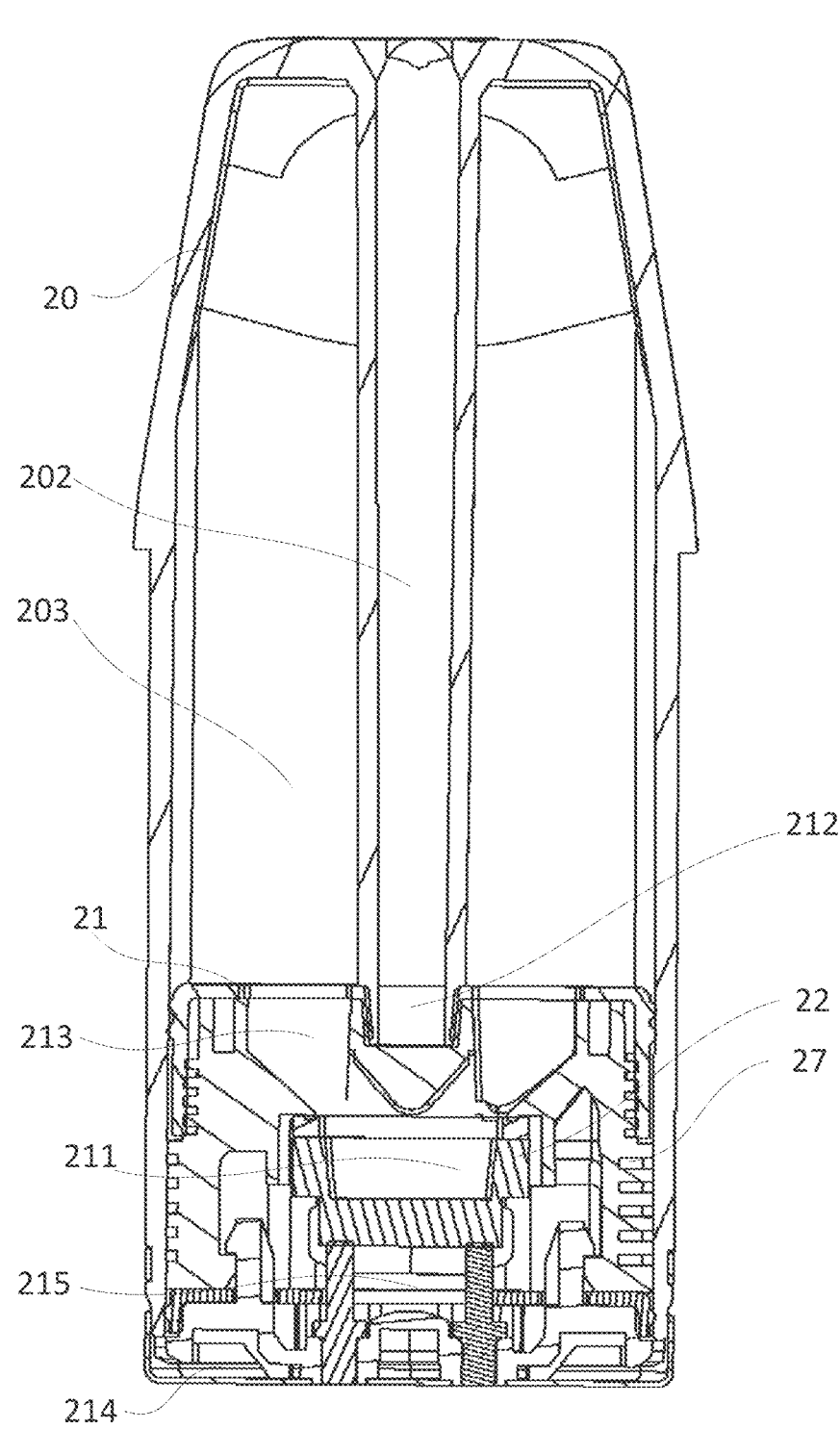
FIG. 3 is a schematic diagram of a cross-sectional structure of the vaporization assembly shown in FIG. 2.

Referring to FIG. 3, the vaporization assembly 200 includes a vaporization housing 20. Specifically, the vaporization housing 20 includes a liquid storage cavity 203 and an air outlet channel 202. The liquid storage cavity 203 is arranged around the air outlet channel 202, and the liquid storage cavity 203 is configured to store the aerosol-generation substrate.

Figure 4:
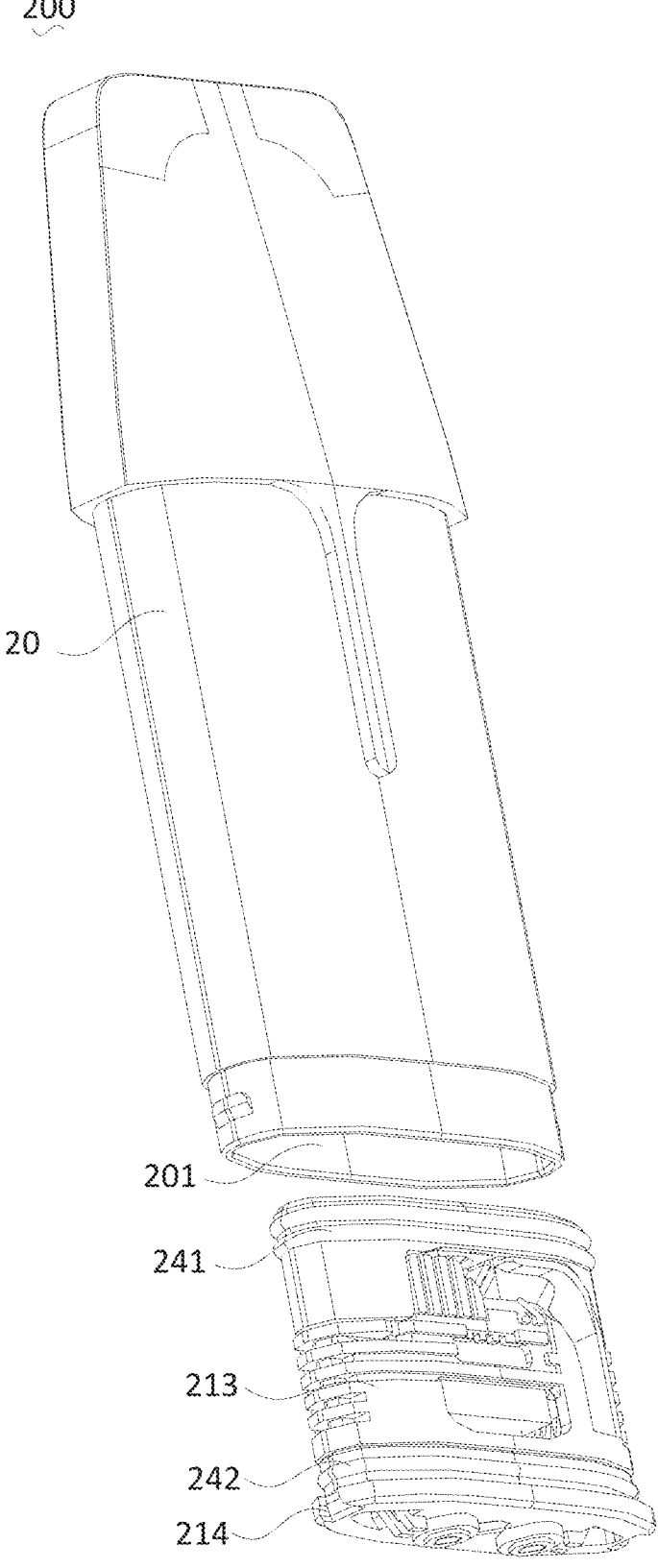
FIG. 4 is a schematic diagram of an exploded structure of the vaporization assembly shown in FIG. 2.

Referring to FIG. 4, the vaporization housing 20 includes an accommodating cavity 201, and the vaporization assembly 200 further includes a vaporization base 21 and a vaporization core 22 that are accommodated in the accommodating cavity 201. The vaporization base 21 includes a vaporization top base 213 and a vaporization bottom base 214. The vaporization bottom base 214 is arranged on a side of the vaporization top base 213 that is away from the liquid storage cavity 203, and cooperates with the vaporization top base 213 to form a mounting cavity 211. The vaporization core 22 is arranged in the mounting cavity 211, and the vaporization core 22 cooperates with a cavity wall of the mounting cavity 211 to define and form a vaporization cavity 215.

Figure 5:
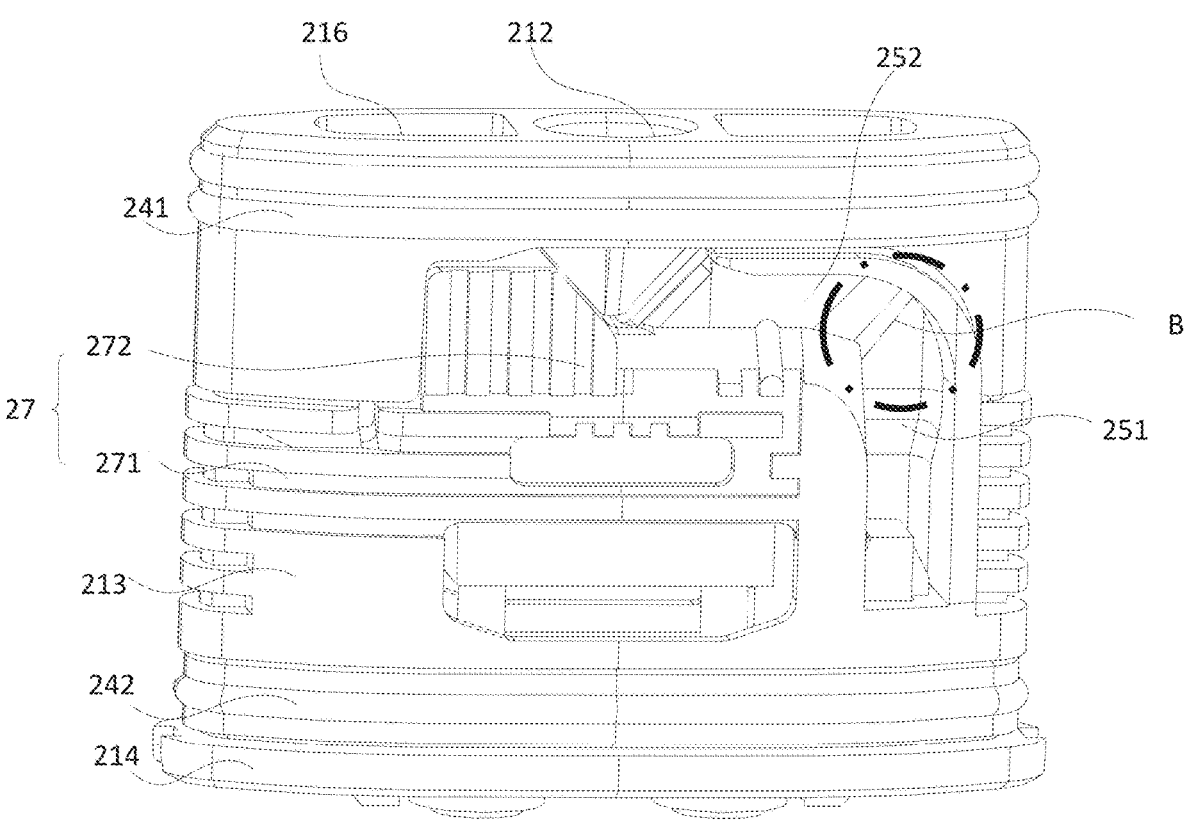
FIG. 5 is a schematic structural diagram of a partial area of the vaporization assembly shown in FIG. 2.

Referring to FIG. 5, the vaporization top base 213 is provided with an air outlet 212 and two liquid flowing channels 216. The two liquid flowing channels 216 are symmetrically arranged on two sides of the air outlet 212 and is in communication between the liquid storage cavity 203 and the vaporization cavity 215. In this way, the aerosol-generation substrate in the liquid storage cavity 203 can enter the vaporization cavity 215 through the two liquid flowing channels 216 to be adsorbed and vaporized by the vaporization core 22. The air outlet channel 202 is in communication with the outside and the air outlet 212, and the air outlet 212 is in communication with the vaporization cavity 215.

In some embodiments, the vaporization assembly 200 further includes a first seal portion 241, and the first seal portion 241 is sealingly connected between an outer side wall of the vaporization top base 213 and an inner side wall of the vaporization housing 20. Specifically, the first seal portion 241 may be made of a silicone material, and the first seal portion 241 is configured to seal the liquid storage cavity 203 to prevent leakage of the aerosol-generation substrate in the liquid storage cavity 203.

In some embodiments, the vaporization assembly 200 further includes a second seal portion 242, and the second seal portion 242 is sealingly connected between an outer side wall of the vaporization bottom base 214 and an inner side wall of the vaporization housing 20. Specifically, the second seal portion 242 can be made of a silicone material, so that the sealing performance of the vaporization assembly 200 to the aerosol and the aerosol-generation substrate can further be ensured.

The vaporization core 22 includes a porous liquid guide member and a heating element. The heating element is arranged on a surface of the porous liquid guide member. The porous liquid guide member guides the aerosol-generation substrate to the heating element by using the capillary force, and is heated and vaporized by the heating element to generate the aerosol. Further, a first airflow channel 251 and a second airflow channel 252 are provided in the vaporization base 21 and are in communication between the vaporization cavity 215 and the air outlet 212.

Referring to FIG. 5, the first airflow channel 251 arranged in the vaporization base 21 in the first direction and the air inlet end of the first airflow channel is in communication with the vaporization cavity 215. Specifically, the first airflow channel 251 is arranged between the vaporization top base 213 and the vaporization bottom base 214 in the first direction. The first direction may be a length direction of the vaporization base 21, and certainly may be other directions, which are not specifically limited in this application. The second airflow channel 252 is arranged in the vaporization base 21 in the second direction and the air outlet end of the second airflow channel 252 is in communication with the air outlet 212. Specifically, the second airflow channel 252 is arranged on the vaporization top base 213 in the second direction. The second direction may be any direction intersecting with the first direction, which is not specifically limited herein in this application. For example, the second direction may be a width direction of the vaporization base 21. The air inlet end of the second airflow channel 252 is in communication with the air outlet end of the first airflow channel 251. During actual use, the aerosol generated by heating in the vaporization cavity 215 can sequentially enter the air outlet channel 202 through the vaporization cavity 215, the first airflow channel 251, the second airflow channel 252, and the air outlet 212, and is finally inhaled by the user.

Further, a corner between the air inlet end of the second airflow channel 252 and the air outlet end of the first airflow channel 251 is a smooth transition corner, as shown in the dotted circle B in FIG. 5. Specifically, there is a smooth transition between a channel wall of the air inlet end of the second airflow channel 252 and a channel wall of the air outlet end of the first airflow channel 251.

In an inhaling process, that is, in a process in which the aerosol flows from the vaporization cavity 215 to the air outlet 212, the aerosol can implement a smooth turning at a communication portion between the air outlet end of the first airflow channel 251 and the air inlet end of the second airflow channel 252, thereby preventing the aerosol from being scattered to form an eddy current or being accumulated to form liquid leakage due to sharp turning, and improving the inhaling experience of the user.

In some embodiments, a smooth rounded corner can be formed between a central axis of the first airflow channel 251 and a central axis of the second airflow channel 252. Specifically, a smooth arc segment is formed at a communication portion between the air outlet end of the first airflow channel 251 and the air inlet end of the second airflow channel 252. In this way, the aerosol can be smoothly turned to the air outlet 212 along the arc segment, avoiding the accumulation of airflow due to the sharp turning, forming the eddy current, and finally causing aerosol residue and liquid leakage, thereby improving the inhaling experience of the user.

Referring to FIG. 3 and FIG. 5, to more effectively prevent the occurrence of liquid leakage, in view of this, the capillary liquid absorbing structure 27 is designed in this embodiment. The capillary liquid absorbing structure 27 is arranged on the vaporization base 21 and is in communication with the second airflow channel 252. The accumulated liquid in the second airflow channel 252 can flow into the capillary absorbing structure 27 under the action of gravity and/or capillary absorbing force and be collected by the capillary absorbing structure 27.

Specifically, in some embodiments, a liquid accumulation notch is dug on the channel wall of the second airflow channel 252 that is away from the liquid storage cavity 203, and the second airflow channel 252 is in communication with the capillary liquid absorbing structure 27 through the liquid accumulation notch. During actual use, under the action of the inhaling force, the accumulated liquid in the second airflow channel 252 can enter the capillary liquid absorbing structure 27 from the liquid accumulation notch to be collected, thereby reducing the accumulated liquid in the second airflow channel 252. Therefore, it is conducive to alleviate the situation of liquid leakage and improve the user experience.

In some embodiments, the capillary liquid absorbing structure 27 includes at least one first capillary groove 271, and the plurality of first capillary grooves 271 are spaced apart on the vaporization base 21 in the first direction. Specifically, the plurality of first capillary grooves 271 may be formed by digging out a part of the outer side wall of the vaporization base 21 at intervals in the first direction, and are all configured to extend in the second direction. In practical application, each first capillary groove 271 can absorb and store accumulated liquid through the capillary force, so as to reduce the accumulated liquid in the second airflow channel 252 and improve the user experience. In some embodiments, the capillary liquid absorbing structure 27 includes at least one second capillary groove 272, and the plurality of second capillary grooves 272 are spaced apart on the vaporization base 21 in the second direction. Specifically, the plurality of second capillary grooves 272 may be formed by digging out a part of the outer side wall of the vaporization base 21 at intervals in the second direction, and are all configured to extend in the first direction. In practical application, each second capillary groove 272 can absorb and store accumulated liquid through the capillary force, so as to reduce the accumulated liquid in the second airflow channel 252 and improve the user experience. It can be understood that the above is only for illustrating the capillary liquid absorbing structure 27, and should not be understood as a limit of this application.

It should be noted that, to cause the aerosol to be more concentrated, in some embodiments, the first airflow channel 251 can be designed to be narrowed to reduce a flowing cross-sectional area of the first airflow channel 251, thereby improving the inhaling experience of the user. Specifically, opposite sides of the vaporization base 21 are separately defined as a first side and a second side. When the first airflow channel 251 is designed to be narrowed, a channel wall of the first airflow channel 251 that is close to the first side can be arranged in a direction close to a channel wall of the second side, so that the first airflow channel 251 can be narrowed.

Referring to FIG. 1 and FIG. 5, the narrowed first airflow channel 251 includes a narrowed space, and a volume of the narrowed space is a volume occupied by the first airflow channel 251 before being narrowed minus a volume occupied by the narrowed first airflow channel 251. Further, the capillary liquid absorbing structure 27 can be arranged on the narrowed space, so that the aerosol can be more concentrated, the space can be fully utilized, and the liquid leakage prevention effect can be improved.

Referring to FIG. 5, in some embodiments, to facilitate the accumulated liquid in the second airflow channel 252 to enter the capillary liquid absorbing structure 27, a liquid guide structure is further designed in this embodiment of this application. The liquid guide structure is arranged on the vaporization base 21, and the accumulated liquid in the second airflow channel 252 flows into the capillary liquid absorbing structure 27 through the liquid guide structure.

Specifically, in some embodiments, the liquid guide structure includes a plurality of airflow guide grooves spaced apart on the vaporization base 21 in the second direction. The liquid inlet end of the airflow guide groove is in communication with the second airflow channel 252, and the liquid outlet end of the airflow guide groove is in communication with the capillary liquid absorbing structure 27. During actual use, when an inhaling action occurs in the air outlet channel 202, the accumulated liquid in the second airflow channel 252 can enter the airflow guide groove from the liquid inlet end of each airflow guide groove, be guided to an area of the capillary liquid absorbing structure 27, and then flow out from the liquid outlet end of each airflow guide groove.

The technical features in the above embodiments may be randomly combined. For concise description, not all possible combinations of the technical features in the embodiment are described. However, provided that combinations of the technical features do not conflict with each other, the combinations of the technical features are considered as falling within the scope recorded in this specification.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:
1. A vaporization assembly, comprising:
a vaporization housing comprising an accommodating cavity, and an air outlet channel in communication with an outside, the air outlet channel extending in a first direction;
a vaporization base comprising a vaporization top base and a vaporization bottom base that form a mounting cavity, the vaporization top base comprising an air outlet, the air outlet of the vaporization top base being in communication with the air outlet channel of the vaporization housing;

a vaporization core arranged in the mounting cavity and cooperating with the vaporization base to define and form a vaporization cavity;

a first airflow channel arranged in the vaporization base in the first direction, an air inlet end of the first airflow channel being in communication with the vaporization cavity; and a second airflow channel arranged in the vaporization base in a second direction intersecting with the first direction, an air outlet end of the second airflow channel being in communication with the air outlet, an air inlet end of the second airflow channel being in communication with an air outlet end of the first airflow channel, wherein a corner between the air inlet end of the second airflow channel and the air outlet end of the first airflow channel comprises a smooth transition corner, wherein the vaporization cavity is in communication with the air outlet of the vaporization top base sequentially through the first airflow channel and the second airflow channel, and wherein the vaporization top base comprises one or more liquid flowing channels.

2. The vaporization assembly of claim 1, wherein a smooth rounded corner is formed between a central axis of the first airflow channel and a central axis of the second airflow channel.

3. The vaporization assembly of claim 1, further comprising:

a capillary liquid absorbing structure arranged on the vaporization base and being in communication with the second airflow channel, wherein accumulated liquid in the second airflow channel flows into the capillary liquid absorbing structure and is collected by the capillary liquid absorbing structure when an inhaling action occurs at the air outlet.

4. The vaporization assembly of claim 3, wherein the capillary liquid absorbing structure comprises at least two first capillary grooves, each first capillary groove of the at least two first capillary grooves being spaced apart on the vaporization base from an adjacent first capillary groove.

5. The vaporization assembly of claim 4, wherein the capillary liquid absorbing structure comprises at least two second capillary grooves, each second capillary groove of the at least two second capillary grooves being spaced apart on the vaporization base from an adjacent second capillary groove.

6. The vaporization assembly of claim 3, further comprising:

a liquid guide structure arranged on the vaporization base, wherein the accumulated liquid in the second airflow channel flows into the capillary liquid absorbing structure through the liquid guide structure.

7. The vaporization assembly of claim 6, wherein the liquid guide structure comprises at least one liquid guide groove, a liquid inlet end of the liquid guide structure being in communication with the second airflow channel, and wherein a liquid outlet end of the liquid guide groove is in communication with the capillary liquid absorbing structure.

8. The vaporization assembly of claim 1, wherein the vaporization base and the vaporization core are accommodated in the accommodating cavity.

9. The vaporization assembly of claim 8, wherein the vaporization core cooperates with a cavity wall of the mounting cavity to define and form the vaporization cavity.

10. The vaporization assembly of claim 9, further comprising:

a first seal portion sealed between an outer side wall of the vaporization top base and an inner side wall of the vaporization housing; and a second seal portion sealed between an outer side wall of the vaporization bottom base and an inner side wall of the vaporization housing.

11. An electronic vaporization device, comprising:

the vaporization assembly of claim 1; and a power supply assembly electrically connected to the vaporization assembly.

12. The vaporization assembly of claim 1, wherein the one or more liquid flowing channels comprises two liquid flowing channels symmetrically arranged on two sides of the air outlet.

13. The vaporization assembly of claim 1, wherein the one or more liquid flowing channels are in communication with the vaporization cavity.

14. The vaporization assembly of claim 13, wherein the one or more liquid flowing channels are in communication between the vaporization cavity and a liquid storage cavity.

15. The vaporization assembly of claim 1, wherein the vaporization housing includes a liquid storage cavity.

16. The vaporization assembly of claim 15, wherein the liquid storage cavity is arranged around the air outlet channel.

17. The vaporization assembly of claim 1, wherein the first airflow channel is arranged between the vaporization top base and the vaporization bottom base.

* * * * *